(12) United States Patent
Hirata et al.

(10) Patent No.: US 8,169,724 B2
(45) Date of Patent: May 1, 2012

(54) OBJECTIVE LENS ADAPTER

(75) Inventors: Tadashi Hirata, Tokyo (JP); Hiroya Fukuyama, Tokyo (JP)

(73) Assignee: Olympus Corporation, Tokyo (JP)

( * ) Notice: Subject to any disclaimer, the term of this patent is extended or adjusted under 35 U.S.C. 154(b) by 381 days.

(21) Appl. No.: 12/488,950

(22) Filed: Jun. 22, 2009

(65) Prior Publication Data

US 2009/0326327 A1 Dec. 31, 2009

(30) Foreign Application Priority Data

Jun. 24, 2008 (JP) ................ 2008-164638

(51) Int. Cl.
G02B 7/02 (2006.01)
(52) U.S. Cl. ...................................... 359/827
(58) Field of Classification Search .......... 359/656, 359/703, 704, 818, 819, 827; 600/175, 176
See application file for complete search history.

(56) References Cited

U.S. PATENT DOCUMENTS 5,584,793 A * 12/1996 Sauer et al. ............ 600/121

FOREIGN PATENT DOCUMENTS

JP SHO 56-85324 A 7/1981

* cited by examiner

Primary Examiner — Joseph P Martinez
(74) Attorney, Agent, or Firm — Scully, Scott, Murphy & Presser, P.C.

(57) ABSTRACT

High-precision observation is made possible while allowing contact between a distal end of an objective lens and an optical element without damaging the distal end of the objective lens and the optical element even when attaching to and detaching from the distal end of the objective lens. Provided is an objective lens adapter including a fixed member that is fixed to a lens tube of an objective lens, a distal-end member including an optical element that is made to be placed in contact with the distal-end surface of the objective lens, and an elastic member that is disposed between the distal-end member and the fixed member and that urges the optical element in a direction that causes the optical element to contact the distal-end surface of the objective lens.

5 Claims, 6 Drawing Sheets

OBJECTIVE LENS ADAPTER

BACKGROUND OF THE INVENTION

1. Field of the Invention

The present invention relates to an objective lens adapter that is attachably/detachably attached to the distal end of an objective lens to protect a front lens of the objective lens.

This application is based on Japanese Patent Application No. 2008-164638, the content of which is incorporated herein by reference.

2. Description of Related Art

Conventionally, an adapter that is attachably/detachably attached to the distal end of an endoscope insertion unit has been known. By attaching this adapter, the field of view can be changed (for example, refer to Japanese Unexamined Patent Application, Publication No. Sho 56-85324).

However, when attaching an adapter to the distal end of an objective lens in a microscope apparatus for conducting high-precision observation of a minute specimen at a high magnification, it is necessary to bring an optical element into contact with the distal end of the objective lens because the optical element needs to be precisely attached. In this case, in particular, when attaching to an objective lens having a small-diameter distal-end portion in which the diameter of the distal-end portion is extremely small for piercing biological tissue such as brains, to observe an organism in vivo, there is a problem in that the distal-end of the objective lens and the optical element may be damaged if an excessive pressing force is applied to the optical element at the time of attachment.

BRIEF SUMMARY OF THE INVENTION

The present invention has been conceived in light of the above-described situation, and an object thereof is to provide an objective lens adapter that makes high-precision observation possible while allowing contact between the distal end of an objective lens and an optical element without damaging the distal end of the objective lens and the optical element, even when attaching the objective lens adapter to and detaching the objective lens adapter from the distal end of the objective lens.

To achieve the above object, the present invention provides the following solutions.

One aspect of the present invention is an objective lens adapter having a fixed member that is fixed to a lens tube of an objective lens, a distal-end member including an optical element that is made to be placed in contact with the distal-end surface of the objective lens, and an elastic member that is disposed between the distal-end member and the fixed member and that urges the optical element in a direction that causes the optical element to contact the distal-end surface of the objective lens.

According to the above-described aspect, by fixing the fixed member to the lens tube while keeping the optical element in contact with the distal-end surface of the objective lens, in a state in which the elastic force of the elastic member is generated, the distal-end member is pulled in a direction close to the fixed member by the elastic force of the elastic member; and thus the state in which the optical element is in contact with the distal-end surface of the objective lens can be maintained. Thus, the problem of damage to the distal-end portion of the objective lens and the optical element can be prevented because the optical element and the distal-end surface of the objective lens are not brought into contact with an excessive pressing force. In addition, it is possible to bring the optical element and the distal-end surface of the objective lens reliably into contact and to precisely position the optical element with respect to the distal-end surface of the objective lens, allowing high-precision observation to be conducted.

The above-described aspect may be configured so that the distal end of the distal-end member is provided with a sharp portion that is inclined with respect to an optical axis.

By doing so, when observing the inside of a specimen by piercing the distal end of the objective lens into the specimen, it is possible to make it easy to pierce the specimen with the distal end of the objective lens due to the sharp portion that is inclined with respect to the optical axis, and it is possible to observe the specimen in a good condition by piercing the specimen with the objective lens without causing excessive damage.

In addition, in the above-described configuration, the optical element may be formed of a prism, which is accommodated in the sharp portion, having a reflection surface that is inclined with respect to the optical axis.

By doing so, it is possible to conduct lateral-view observation of the specimen disposed in a direction intersecting the optical axis of the objective lens by bending the optical axis at the reflection surface of the prism. Because the sharp portion is inclined with respect to the optical axis, the prism having a reflection surface inclined with respect to the optical axis can be disposed fittingly into the internal space formed by the sharp portion.

In addition, in the above-described aspect, the reflection surface may be provided with a reflection film.

By doing so, the reflection efficiency at the reflection surface of the prism can be improved. By providing the reflection film on the reflection surface of the prism, the reflectivity is not reduced even though the reflection surface is exposed and comes in contact with the specimen, and thus, it is possible to conduct observation with a bright image.

In addition, in the above-described aspect, it is preferable that a cover member that covers the reflection surface be disposed, and a concave portion that forms an air layer be provided on a surface of the cover member opposing the reflection surface.

By doing so, the specimen does not come in contact with the reflection surface even when piercing the specimen with the distal-end member, and it is possible to totally reflect light at the reflection surface due to the air layer formed by the concave portion. The reflection efficiency improves as a result, and it is possible to conduct observation with a bright image. In addition, the optical element can be protected by covering the reflection surface of the optical element with the cover member.

According to the present invention, an advantage is afforded in that high-precision observation is made possible while allowing contact between a distal end of the objective lens and an optical element without damaging the distal end of the objective lens and the optical element even when attaching the objective lens adapter to the distal end of the objective lens and detaching the objective lens adapter therefrom.

DETAILED DESCRIPTION OF THE INVENTION

An objective lens adapter according to an embodiment of the present invention will be described below referring to FIGS. 1 to 5.

Figure 2:
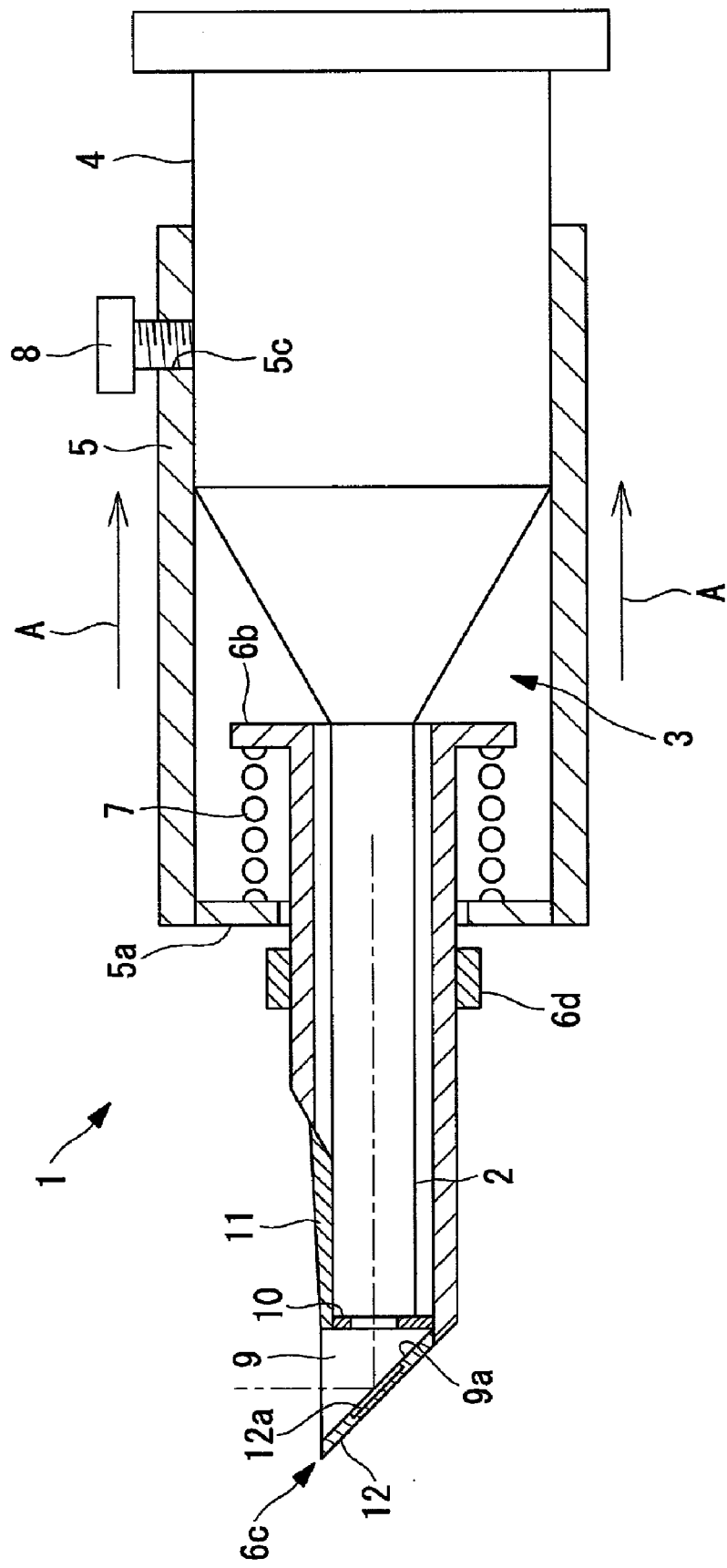
FIG. 2 is a longitudinal sectional view explaining a state in which the objective lens adapter in FIG. 1 is attached to a distal end of an objective lens.

As shown in FIG. 2, an objective lens adapter 1 according to this embodiment, which is an objective lens adapter 1 that is attachably/detachably attached to an objective lens 3 for in vivo observation and that has a small-diameter distal-end portion 2, is provided with a fixed member 5 that is fixed to a lens tube 4 of the objective lens 3, a distal-end member 6 that is disposed so as to cover the small-diameter distal-end portion 2 of the objective lens 3, and a compression coil spring (elastic member) 7 that is disposed between the distal-end member 6 and the fixed member 5.

The fixed member 5 is formed substantially cylindrically, has an inside diameter that allows it to fit on the lens tube 4 of the objective lens 3, and has an inner-rib like inner flange portion 5a on one end extending radially inward. The inner flange portion 5a is provided with a through-hole 5b that penetrates in the axial direction.

The fixed member 5 can be fixed onto the lens tube 4 of the objective lens 3 by friction from pressing the distal end of a set screw 8, which is screwed into a threaded hole 5c penetrating in the radial direction thereof, against the external surface of the lens tube 4 of the objective lens 3.

The distal-end member 6 is provided with a substantially cylindrical tubular portion 6a, a prism (optical element) 9 fixed on one end of the tubular portion 6a, and an outer-rib like outer flange portion 6b that extends radially outward on the other end of the tubular portion 6a. The tubular portion 6a has an outside diameter slightly smaller than the inside diameter of the through-hole 5b of the inner flange portion 5a. In addition, the outer flange portion 6b has an outside diameter sufficiently larger than the inside diameter of the through hole 5b. Reference sign 6d in the drawings is a stopper that sets the position of the distal-end member 6 to a predetermined position with respect to the fixed member 5.

Figure 3:
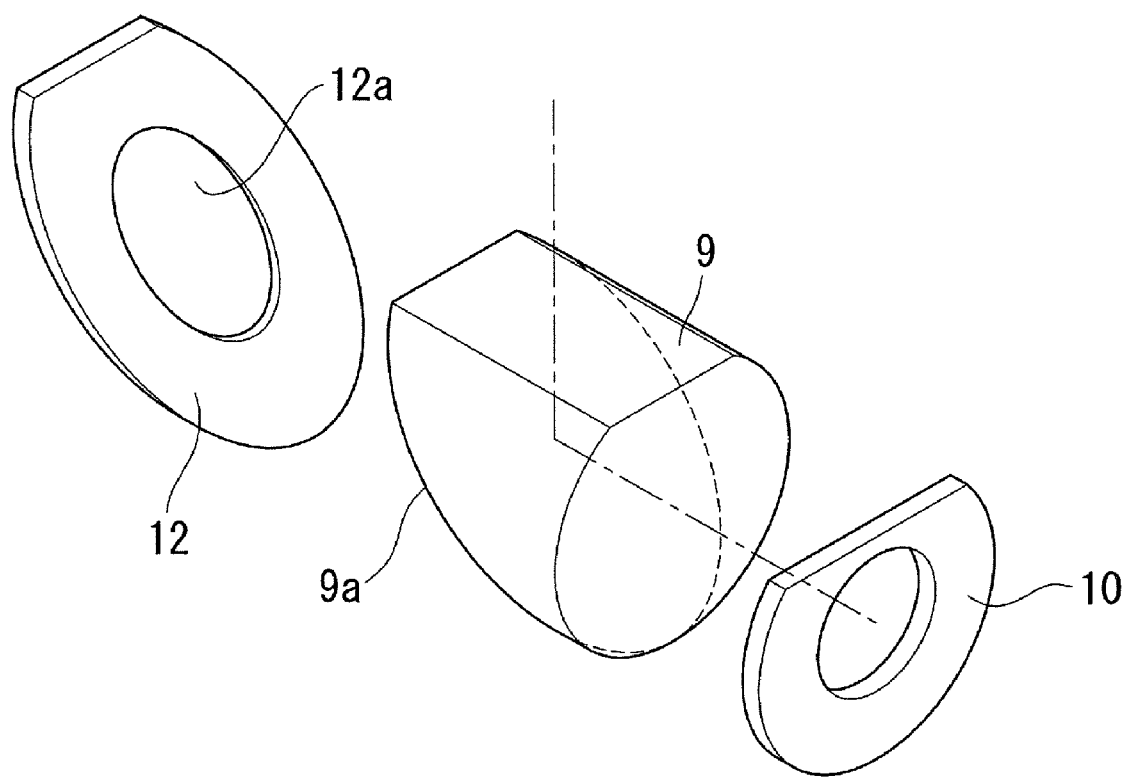
FIG. 3 is an exploded perspective view showing a prism, a cover member, and a spacer accommodated in a distal-end member of the objective lens adapter in FIG. 1.

The tubular portion 6a has a sharp portion 6c whose distal end is in a cut-off configuration at a 45° angle with respect to the axis line. The prism 9 is formed in a columnar shape as shown in FIG. 3 and has a reflection surface 9a inclined at 45° with respect to the axis line. The prism 9 is fittingly accommodated in the sharp portion 6c at the distal end of the tubular portion 6a.

Figure 4:
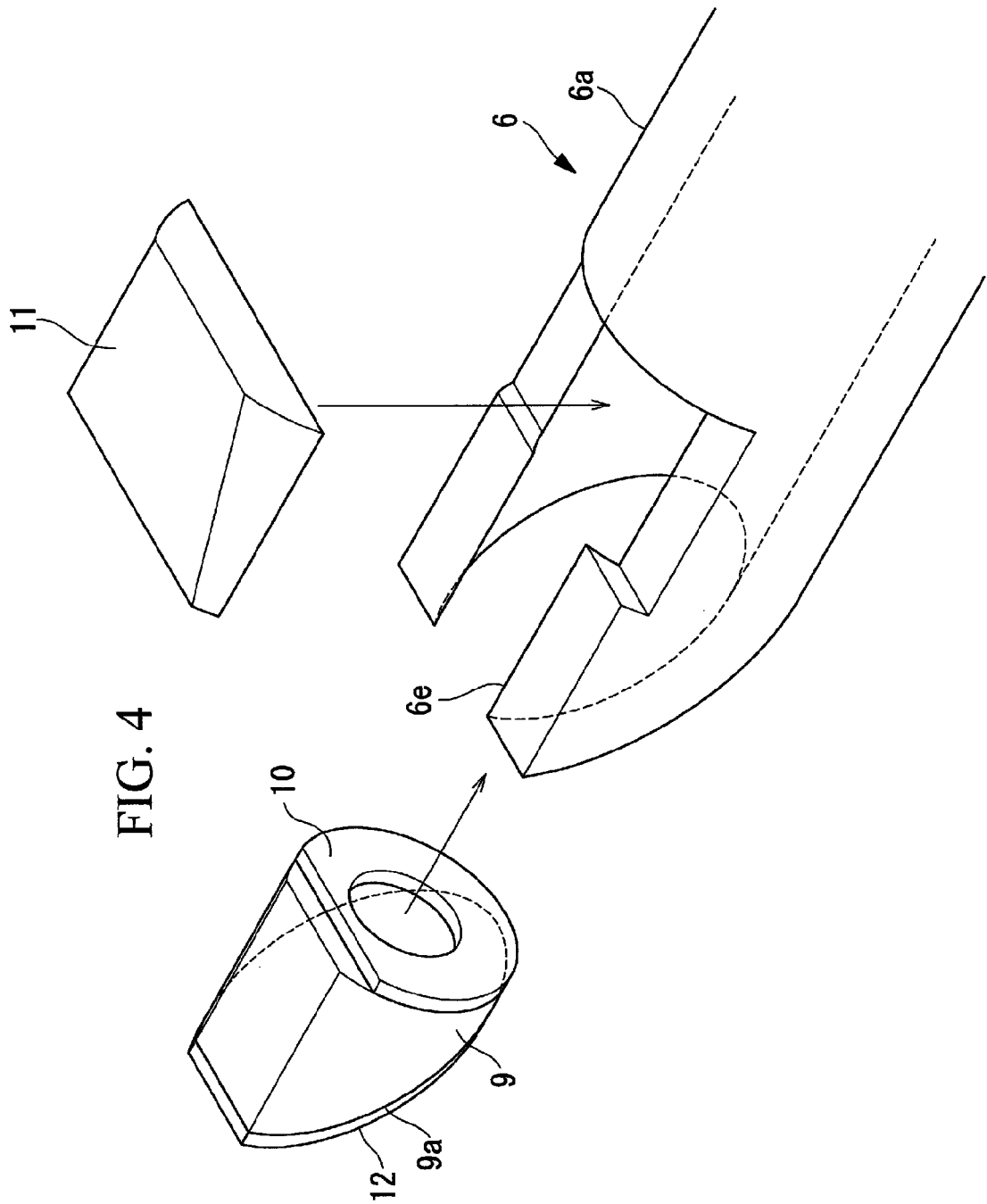
FIG. 4 is an exploded perspective view showing a state in which the prism, the cover member, and the spacer in FIG. 3 are to be accommodated in the distal-end member and a plate member is to be attached.

As shown in FIGS. 3 and 4, a ring shaped spacer 10 whose thickness is controlled is disposed on the surface of the prism 9 inside the tubular portion 6a.

By inserting the spacer 10, direct contact between the prism 9 and a lens (not shown) at the distal end of the objective lens 3 is avoided, thereby preventing damage to the prism 9 and the lens at the distal end of the objective lens 3.

Figure 5:
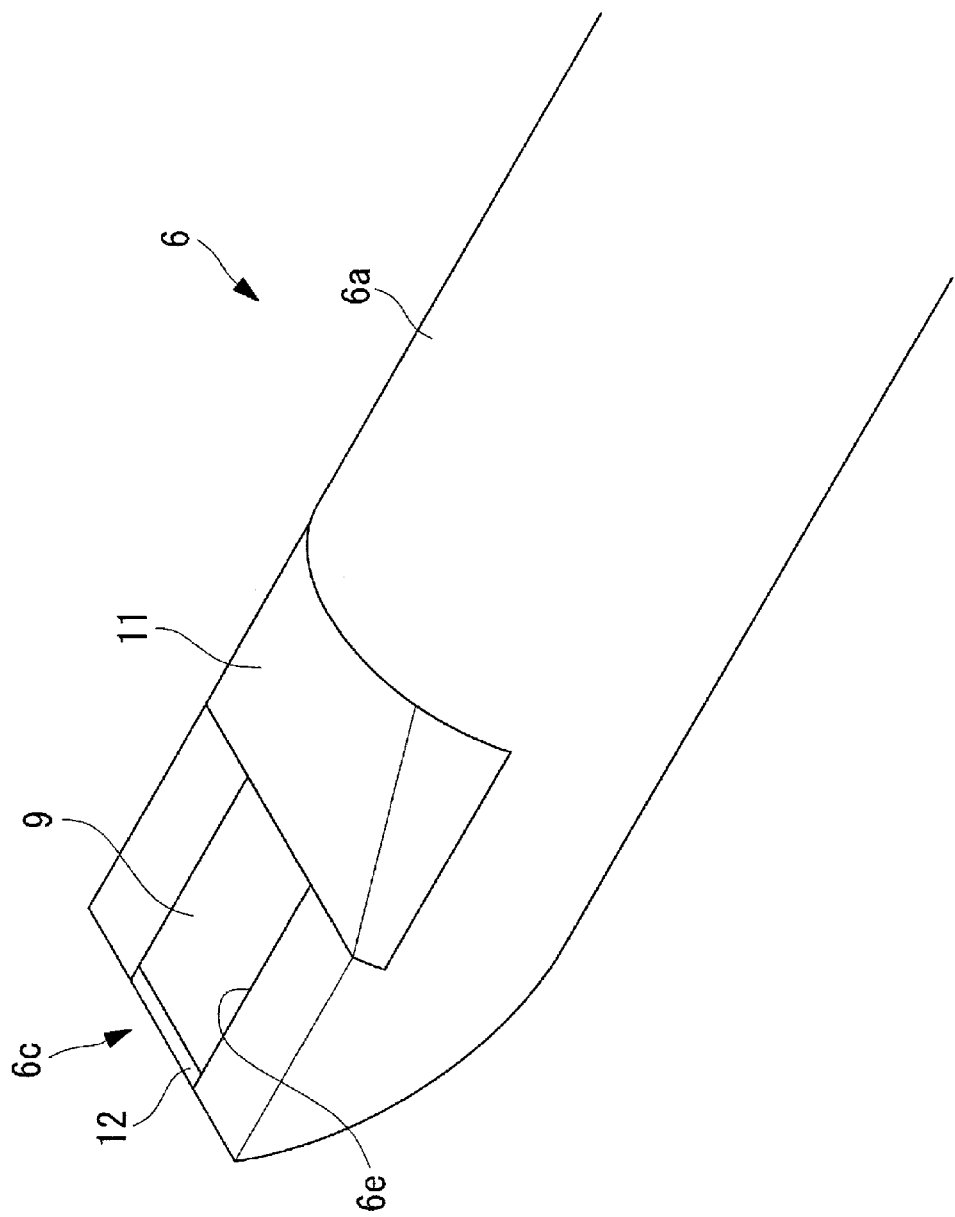
FIG. 5 is a perspective view showing a distal-end portion of the distal-end member of the objective lens adapter in FIG. 1.

In addition, as shown in FIGS. 4 and 5, a part of the side wall of the tubular portion 6a is cut away on the side of the sharp portion 6c, exposing the prism 9 accommodated inside.

In addition, so as not to form a large level difference between the surface of the prism 9 exposed to the outside and the tubular portion 6a, the side wall of the tubular portion 6a is also cut away in an area continuous with the prism 9 and is sealed by bonding a plate portion 11 whose plate thickness gradually increases.

Figure 1:
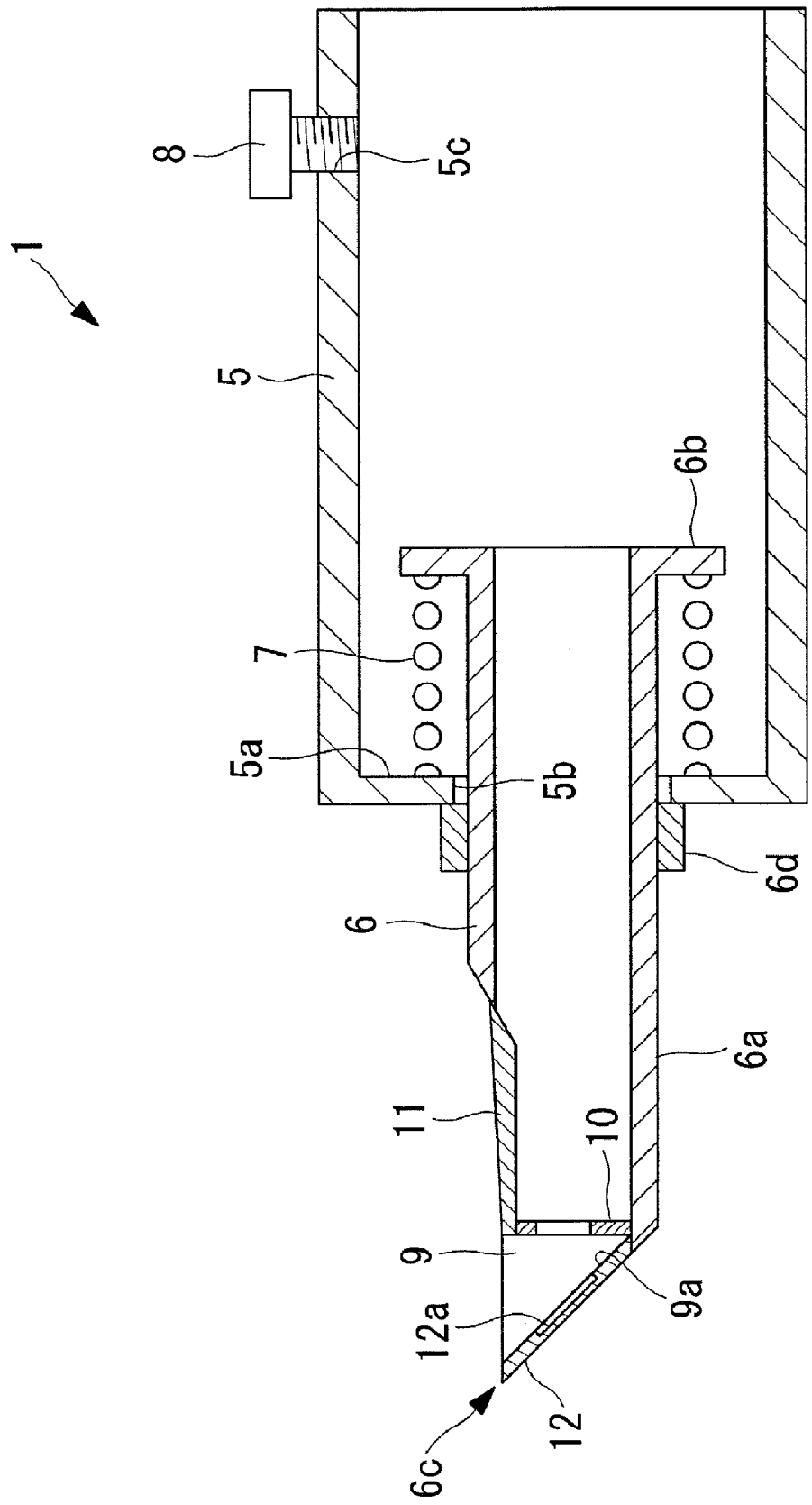
FIG. 1 is a longitudinal sectional view showing an objective lens adapter according to an embodiment of the present invention.

The reflection surface 9a is covered by a cover member 12, and, as shown in FIGS. 1 to 3, the surface of the cover member 12 opposing the reflection surface 9a is provided with a concave portion 12a close to the center position thereof.

By disposing the concave portion 12a opposite the reflection surface 9a of the prism 9, an air layer can be formed on the back surface side of the reflection surface 9a, and thus total reflection of light at the reflection surface 9a is possible.

By having the tubular portion 6a penetrate the through-hole 5b, the compression coil spring 7 is disposed in a position sandwiched in the axial direction between the outer flange portion 6b disposed inside the fixed member 5 and the inner flange portion 5a of the fixed member 5. Thus, by relatively moving the fixed member 5 and the distal-end member 6 in the axial direction, the amount of elastic deformation of the compression coil spring 7 is changed, causing mutual elastic forces to act.

The operation of the thus-configured objective lens adapter 1 according to this embodiment will be described below.

To attach the objective lens adapter 1 according to this embodiment to the distal end of the objective lens 3 having the small-diameter distal-end portion 2, the fixed member 5 and the distal-end member 6 of the objective lens adapter 1 are placed thereon from the small-diameter distal-end portion 2 side of the objective lens 3 to bring the prism 9 into contact with the distal-end surface of the small-diameter distal-end portion 2 via the spacer 10.

From this state, the fixed member 5 is moved with respect to the distal-end member 6, in a direction indicated by an arrow A in FIG. 2, toward the proximal end of the objective lens 3; thereby the compression coil spring 7 sandwiched between the outer flange portion 6b of the distal-end member 6 and the inner flange portion 5a of the fixed member 5 is compressed, generating an elastic force. Then, the set screw 8 provided on the fixed member 5 is screwed into the threaded hole 5c in a state wherein the compression coil spring 7 is elastically deformed enough to obtain a predetermined elastic force; the fixed member 5 can be fixed in that position by pressing the distal end of the set screw 8 against the external surface of the lens tube 4 of the objective lens 3.

By doing so, the prism 9 can be precisely positioned with respect to the objective lens 3 because the state in which the prism 9 is pressed onto the distal end of the small-diameter distal-end portion 2 via the spacer 10 is maintained by means of the elastic force of the compression coil spring 7. In addition, generation of an excessive pressing force is prevented because the pressing is achieved by means of the elastic force of the compression coil spring 7, and thus occurrence of the problem of the small-diameter distal-end portion 2 of the objective lens 3 and the prism 9 being damaged can be proactively prevented.

In particular, in the case of the objective lens 3 for observing the internal condition of brain tissue, the small-diameter distal-end portion 2 is extremely thin, and therefore, attachment/detachment by screws tends to apply an excessive pressing force; however, an advantage of this embodiment is that there is no such problem.

With the objective lens adapter 1 according to this embodiment, attached to the distal end of the objective lens 3 in this way, it is possible to simplify the procedure of piercing biological tissue with the sharp portion 6c provided on the distal end. In other words, whereas a part of the biological tissue is crushed when piercing with the small-diameter distal-end portion 2 of an objective lens 3 with a flat distal end as it is, causing severe damage, according to this embodiment, there is an advantage in that, due to the sharp portion 6c, the objective lens 3 can pierce the biological tissue without inflicting damage.

In addition, because the side wall adjacent to the sharp portion 6c is cut away to expose a part of the prism 9, when piercing the biological tissue, the biological tissue can be brought into contact with the exposed surface of the prism 9. Furthermore, because the objective lens adapter 1 is configured so as not to form a level difference between the surface of the prism 9 and the external surface of the tubular portion 6a, when piercing the biological tissue, the problem of the biological tissue being scraped by the level difference thereby inflicting damage can be prevented.

Then, the illumination light guided from the objective lens 3 side is emitted from the small-diameter distal-end portion 2, is incident on the prism 9, is deflected 90° at the reflection surface 9a of the prism 9, and thus the illumination light is radiated onto the biological tissue in contact with the surface of the prism 9 from a notch 6e provided in the tubular portion 6a. In the case where the illumination light is excitation light, the illumination light excites a fluorescent substance that exists in the biological tissue, generating fluorescence, and the generated fluorescence returns along the same path to be collected by the objective lens 3.

In this case, because the cover member 12, disposed so as to cover the reflection surface 9a of the prism 9, has the concave portion 12a that forms the air layer with the prism 9, it is possible to bring about total reflection of light at the reflection surface 9a. As a result, reduction of the intensity of the illumination light radiated onto the biological tissue and the detected light, such as fluorescence obtained from the biological tissue, is prevented; the illumination efficiency and the detection efficiency are improved; and it is thus possible to conduct observation with a bright image.

In addition, with the objective lens adapter 1 according to this embodiment, when conducting multiple observations of the same site with time intervals therebetween, after conducting an observation with the objective lens 3, having the objective lens adapter 1 attached thereto, piercing biological tissue, the set screw 8 is loosened to release the fixing of the fixed member 5 to the lens tube 4 of the objective lens 3, thereby making it possible to withdraw the objective lens 3 from the objective lens adapter 1 while leaving the objective lens adapter 1 piercing the biological tissue. Then, to resume observation, the objective lens 3 may be inserted into and fixed to the objective lens adapter 1 that pierces the biological tissue.

Note that, in this embodiment, the sharp portion 6c, which is shaped as if the distal end of the tubular portion 6a is cut off at an angle, is provided, and the prism 9, having the reflection surface 9a inclined at 45°, is disposed inside; however, instead, a prism 9 having a reflection surface 9a inclined at an angle other than 45° may be adopted. Although the cover member 12 having the concave portion 12a opposing the reflection surface 9a of the prism 9 is provided, instead, a metallic thin film, a dielectric multilayer film, etc., may be formed on the reflection surface 9a. In this case, the reflection efficiency becomes lower than in the case of total reflection, but it is advantageous in that the cover member 12 and the concave portion 12a are not necessary.

In addition, although the prism 9 having the reflection surface 9a is adopted as an optical element in this embodiment, instead, a glass flat plate member that transmits light in the optical axis direction may be adopted. By doing so, the working distance can be adjusted to the optimal position.

Figure 6:
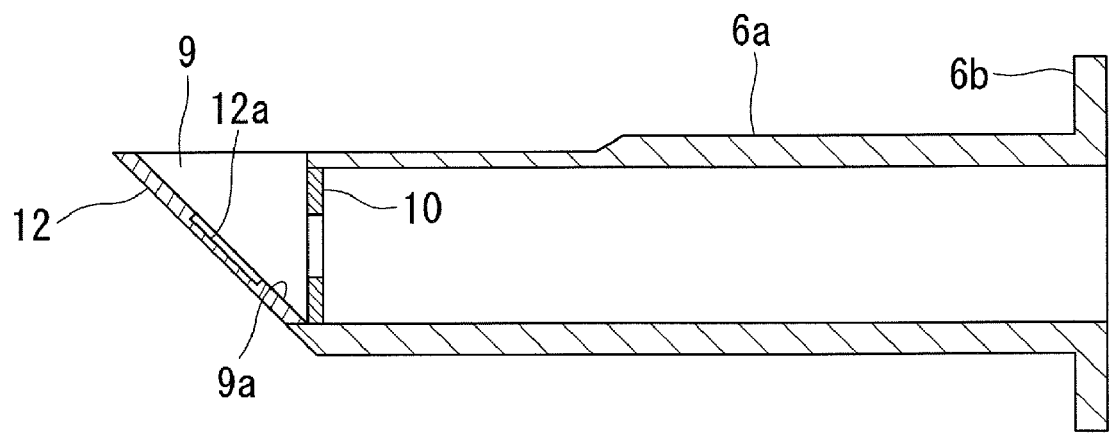
FIG. 6 is a longitudinal sectional view showing a first modification of the distal-end member of the objective lens adapter in FIG. 1.
Figure 7:
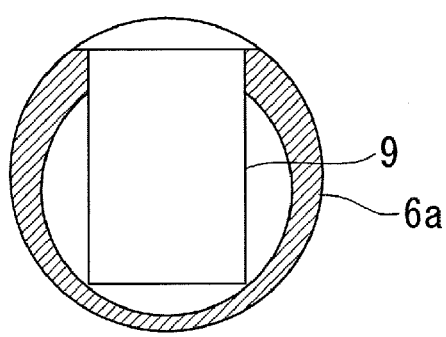
FIG. 7 is a cross-sectional view showing a second modification of the distal-end member of the objective lens adapter in FIG. 1.

In addition, although the columnar prism 9 is accommodated in the cylindrical tubular portion 6a, instead, a triangular prism (not shown) may be employed, and an accommodation portion may be formed at the distal end of the tubular portion 6a in such a shape that the triangular prism can be accommodated therein. Further, when using the triangular prism, as shown in FIG. 6, the plate member 11 may be omitted by providing a thick-walled tubular portion 6a. Additionally, as shown in FIG. 7, the plate member 11 may be omitted while keeping the outside diameter small by decentering the inside diameter and outside diameter of the tubular portion thereby forming a thick-walled portion.

What is claimed is:

1. An objective lens adapter comprising:
   a fixed member that is fixed to a lens tube of an objective lens;
   a distal-end member including an optical element that is made to be placed in contact with a distal-end surface of the objective lens; and
   an elastic member that is disposed between the distal-end member and the fixed member and that urges the optical element in a direction that causes the optical element to contact the distal-end surface of the objective lens.

2. The objective lens adapter according to claim 1, wherein the distal end of the distal-end member is provided with a sharp portion that is inclined with respect to an optical axis.

3. The objective lens adapter according to claim 2, wherein the optical element is formed of a prism, which is accommodated in the sharp portion, having a reflection surface that is inclined with respect to the optical axis.

4. The objective lens adapter according to claim 3, wherein the reflection surface is provided with a reflection film.

5. The objective lens adapter according to claim 3, wherein a cover member that covers the reflection surface is disposed, and a concave portion that forms an air layer is provided on a surface of the cover member opposing the reflection surface.

\* \* \* \* \*